United States Patent [19]

Moniot et al.

[11] Patent Number: 4,704,457

[45] Date of Patent: Nov. 3, 1987

[54] PROCESS FOR THE PREPARATION OF (3S)-3-[[[2-(PROTECTED AMINO)-4-THIAZOLYL]-OXOACETYL-]AMINO]-2-OXO-1-AZETIDINESULFONIC ACID AND 4-SUBSTITUTED DERIVATIVES THEREOF

[75] Inventors: Jerome L. Moniot, Chester; Christopher M. Cimarusti, Pennington; Rita T. Fox, Princeton, all of N.J.

[73] Assignee: E. R. Squibb & Sons, Inc., Princeton, N.J.

[21] Appl. No.: 390,728

[22] Filed: Jun. 21, 1982

[51] Int. Cl.$^4$ .................. C07D 417/12; C07B 43/06; C07B 41/06
[52] U.S. Cl. .................. 540/355; 540/225; 540/227; 540/316
[58] Field of Search .................. 260/245.4

[56] References Cited

U.S. PATENT DOCUMENTS 4,166,115  8/1979  Takaya et al. .................. 424/246
4,303,655  12/1981  Kamiya et al. .................. 544/27

FOREIGN PATENT DOCUMENTS 2071650  9/1981  United Kingdom .

*Primary Examiner*—Mark L. Berch
*Attorney, Agent, or Firm*—Lawrence S. Levinson; Donald J. Barrack

[57] ABSTRACT

A compund having the formula

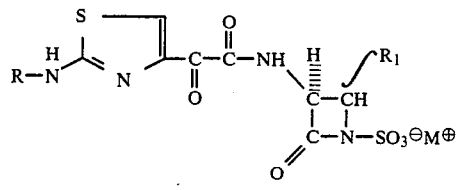

can be prepared by coupling a compound having the formula

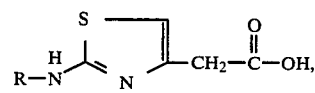

or a salt thereof, with a compound having the formula

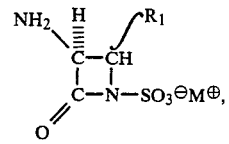

to yield a compound having the formula

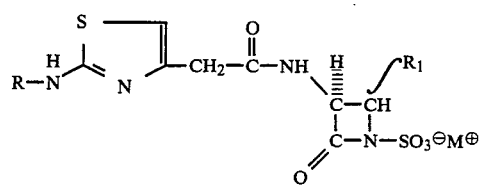

and oxidizing that compound to yield the desired compound; wherein
R is hydrogen or an amino protecting group;
$R_1$ is hydrogen, methly or ethyl;
$M^\oplus$ is an inorganic cation or a substituted ammonium ion; and
$M_1^\oplus$ is hydrogen, an organic cation, or a substituted ammonium ion.

5 Claims, No Drawings

PROCESS FOR THE PREPARATION OF (3S)-3-[[[2-(PROTECTED AMINO)-4-THIAZOLYL]-OXOACETYL]AMINO]-2-OXO-1-AZETIDINESULFONIC ACID AND 4-SUBSTITUTED DERIVATIVES THEREOF

RELATED APPLICATION

U.S. patent application Ser. No. 344,895, filed Feb. 1, 1982, U.S. Pat. No. 4,443,374 discloses a process for the preparation of (3S)-3-[[(2-amino-4-thiazolyl)[(1-carboxy-1-methylethoxy)imino]acetyl]amino]-2-oxo-1-azetidinesulfonic acid and 4-substituted derivatives thereof.

BACKGROUND OF THE INVENTION

United Kingdom patent application No. 2,071,650, publiced Sept. 23, 1981, discloses β-lactam antibiotics including (3S)-3-[[(2-amino-4-thiazolyl)[(1-carboxy-1-methylethoxy)imino]acetyl]amino]-2-oxo-1-azetidinesulfonic acid and 4-substituted derivatives thereof.

BRIEF DESCRIPTION OF THE INVENTION

This invention is directed to a process for the preparation of (3S)-3-[[[2-(protected amino)-4-thiazolyl]oxoacetyl]amino]-2-oxo-1-azetidinesulfonic acid and 4-substituted derivatives thereof. The process of this invention can be represented diagramatically as follows:

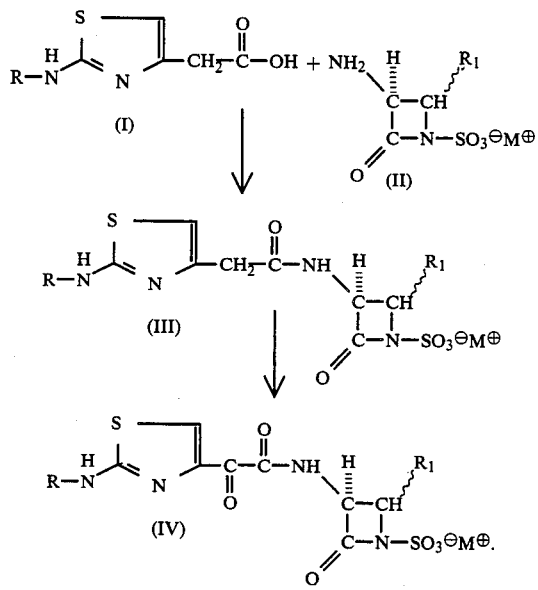

The ketoamides of formula IV are useful as intermediates for the preparation of (3S)-3-[[(2-amino-4-thiazolyl)[(1-carboxy-1-methylethoxy)imino]acetyl]amino]-2-oxo-1-azetidinesulfonic acid and 4-substituted derivatives thereof; i.e., compounds having the formula

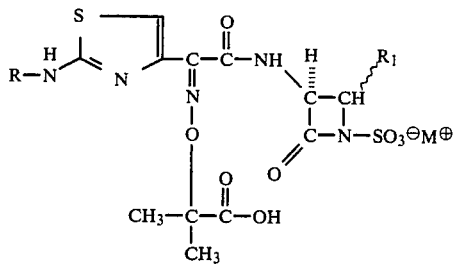

In the above formulas, and throughout the specification, the symbols are as defined below.

R is hydrogen or an amino protecting group;
R₁ is hydrogen, methyl or ethyl;
M⊕ is an inorganic cation or a substituted ammonium ion; and
M₁⊕ is hydrogen, an inorganic cation, or a substituted ammonium ion.

The term "amino protecting group" refers to any group which will protect the nitrogen atom to which it is attached from reacting in the above sequence, and which, at the end of the above-described reaction sequence, can be cleaved from the nitrogen atom under conditions that do not alter the rest of the molecule. Exemplary amino protecting groups are triphenylmethyl, formyl, t-butoxycarbonyl, benzyloxycarbonyl, 1,1-dimethylpropoxycarbonyl, allyloxycarbonyl, and

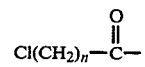

wherein n is 1 to 4, preferably 1 or 4.

The term "inorganic cation" refers to any positively charged inorganic atom or group of atoms. Exemplary inorganic cations are the alkali metals (e.g., lithium, sodium and potassium), the alkaline earth metals (e.g., calcium and magnesium), manganic, ferrous, cobalt, thallium, manganous, and ammonium (NH₄⊕).

The term "substituted ammonium ion" refers to organic cations; the tri- and tetra-substituted ammonium ions are specifically contemplated. Exemplary substituted ammonium ions are the pyridinium, triethylammonium, and tetrabutylammonium salts.

DETAILED DESCRIPTION OF THE INVENTION

The process of this invention yields intermediates which can be used to prepare compounds of formula V. Those compounds of formula V wherein R is other than hydrogen can be deprotected to yield the corresponding compound of formula V wherein R is hydrogen. As described in United Kingdom patent application No. 2,071,650, published Sept. 23, 1981, compounds of formula V are β-lactam antibiotics useful for combating bacterial infections (including urinary tract infections and respiratory infections) in mammalian species, such as domesticated animals and humans. It is further disclosed that for combating bacterial infections in mammals, a compound of formula V can be administered to a mammal in need thereof in an amount of about 1.4 mg/kg/day to about 350 mg/kg/day, preferably about 14 mg/kg/day to about 100 mg/kg/day.

The reaction of an aminothiazolylacetic acid of formula I, or a salt thereof, and a (3S)-3-amino-2-oxo-1- azetidinesulfonic acid salt of formula II proceeds most readily if the aminothiazolylacetic acid of formula I is in an activated form. Activated forms of carboxylic acids are well known in the art and include acid halides, acid anhydrides (including mixed acid anhydrides), activated acid amides and activated acid esters. Mixed acid anhydrides for use in the process of this invention can be formed from an acetic acid derivative of formula I and a substituted phosphoric acid (such as dialkoxyphosphoric acid, dibenzyloxyphosphoric acid or diphenoxyphosphoric acid), a substituted phosphinic acid (such as diphenylphosphinic acid or dialkylphosphinic acid), dialkylphosphorous acid, sulfurous acid, thiosulfuric acid, sulfuric acid, a carboxylic acid such as 2,2-dimethylpropanoic acid, a carboxylic acid halide such as 2,2-dimethylpropanoyl chloride, and others. Examplary of the activated amides which can be used in the process of this invention are those formed from an acetic acid derivative of formula I and imidazole, 4-substituted imidazoles, dimethylpyrazole, triazole, tetrazole or dimethylaminopyridine. Exemplary of the activated esters which can be used in the process of this invention are the cyanomethyl, methoxymethyl, dimethyliminomethyl, vinyl, propargyl, 4-nitrophenyl, 2,4-dinitrophenyl, trichlorophenyl, pentachlorophenyl, mesylphenyl, phenylazophenyl, phenylthio, 4-nitrophenylthio, p-cresylthio, carboxymethylthio, pyranyl, pyridyl, piperidyl, and 8-quinolylthio esters. Additional examples of activated esters are esters with an N-hydroxy compound such as N,N-dimethylhydroxylamine, 1-hydroxy-2(1H)pyridone, N-hydroxysuccinimide, N-hydroxyphthalimide, and 1-hydroxy-6-chloro-1H-benzotriazole.

The amides of formula III, which result from the coupling of an aminothiazolyl acetic acid of formula I (or a salt thereof) and a (3S)-3-amino-2-oxo-1-azetidinesulfonic acid salt of formula II can be oxidized to yield the corresponding ketoamide of formula IV. A wide variety of oxidation procedures may be used. An exemplary procedure comprises oxidation of an amide of formula III by treatment with potassium nitrosodisulfonate in water, or a mixed aqueous system. Alternatively, oxidation can be accomplished by treatment of an amide of formula III with selenium dioxide in an inert solvent (e.g., dioxane). The oxidation can also be accomplished by the use of metal catalysts in the presence of a suitable co-oxidant. Such combinations include platinum, palladium and other noble metals with air or oxygen as co-oxidant; cupric ion in solution with air or persulfate ion as co-oxidant; ferrous ion in solution with hydrogen peroxide as co-oxidant; and manganic ion, cobalt ion, thallium ion and other transition metal ions with air or oxygen gas as co-oxidant. The preferred method of oxidation of an amide of formula III comprises treatment with a solution of manganic ion in a suitable solvent, such as acetic acid, in the presence of air or oxygen as co-oxidant.

As described in copending U.S. patent application Ser. No. 344,895, filed Feb. 1, 1982 a ketoamide of formula IV can be condensed in water or in an organic solvent, with 2-aminooxy-2-methylpropanoic acid, or a salt thereof, selectively yielding the corresponding syn-oxime of formula V. If the pH of the condensation reaction mixture is far to the acid side (i.e., about 2.5 or less), the syn-oxime of formula V will be in the form of the zwitterion (i.e., $M_1^{\oplus}$ is hydrogen). If the pH of the condensation reaction mixture is more than about 3.2, the syn-oxime of the formula V will be a salt corresponding to the salt of formula IV (i.e., $M_1^{\oplus}$ in formula V is the same as $M^{\oplus}$ in formula IV).

The [2-(protected amino)-4-thiazolyl]acetic acid compounds of formula I are readily obtained using conventional procedures by protection of the amino group of 2-amino-4-thiazolylacetic acid; see, for example, U.S. Pat. No. 4,008,246. The (3S)-3-amino-2-oxo-1-azetidinesulfonic acids of formula II are described in the literature; see, for example, United Kingdom patent application No. 2,071,650, published Sept. 23, 1981.

The following examples are specific embodiments of this invention.

EXAMPLE 1

(3S-trans)-3-[[[2-(Formylamino)-4-thiazolyl]oxoacetyl]amino]-4-methyl-2-oxo-1-azetidinesulfonic acid, potassium salt (A) 2-Formylamino-4-thiazolylylacetic acid In a 3-neck flask fitted with a thermometer, reflux condenser and argon inlet was placed acetic anhydride (36 ml) and formic acid 98% (16 ml) and the mixture was heated to 60° C. for 90 minutes. To this solution was then added glacial acetic acid (50 ml) which caused a drop in temperature to ca. 40° C., and then 2-amino-4-thiazolylacetic acid (47.1 g) is added in 3 portions over 5 minutes. The temperature rose to ca. 60° C., was cooled to 40° C. and the reaction mixture was then stirred at 40° C. for 90 minutes. The solution was then cooled to 15° C., diluted with water (200 ml) and stirred at 15° C. for 20 minutes. The resulting solid was removed by filtration, washed with cold water (0°-5° C.) and dried under vacuum to give 45 g of the title compound as a powder, melting point 195°-198° C.

(B) (3S-trans)-3-[[[2-(Formylamino)-4-thiazolyl]acetyl]amino]-4-methyl-2-oxo-1-azetidinesulfonic acid, potassium salt To a solution of pyridine (9.6 ml) and methylene chloride (150 ml) in a 1-liter flask equipped with mechanical stirring and thermometer and pre-chilled to −15° C. was added a solution of pivaloyl chloride (15 ml) in methylene chloride (15 ml) at a rate to maintain a temperature below −10° C. After 2 minutes, a pre-chilled solution (−15° C.) of 2-formylamino-4-thiazolylacetic acid (22.5 g) and triethylamine (18.3 ml) in methylene chloride (240 ml) was added at a rate to maintain an internal temperature of below −5° C. After 5 minutes, a prechilled solution (−15° C.) of (3S-trans)-3-amino-4-methyl-2-oxo-1-azetidinesulfonic acid (21.6 g) and triethylamine (18 ml) in acetonitrile (180 ml) was added at a rate to control internal temperature below 0° C. The reaction mixture was cooled to and maintained at −10° C. for 90 minutes. The reaction was concentrated under reduced pressure to a volume of 150 ml and was then diluted with absolute ethanol to 750 ml. With mechanical stirring a 10% ethanolic potassium acetate solution (225 ml) was added. The resulting precipitate was stirred at −15° C. for 20 minutes, filtered under a nitrogen atmosphere, washed with two 200 ml portions of cold absolute ethanol and dried at 40° C. under vacuum to give 44.35 g of the title compound containing 1 mole of water of crystallization.

(C)
(3S-trans)-3-[[[2-(Formylamino)-4-thiazolyl]oxoacetyl]amino]-4-methyl-2-oxo-1-azetidinesulfonic acid, potassium salt A mixture of acetic acid (50 ml), acetic anhydride (12 ml) and manganese diacetate tetrahydrate (6.32 g, 0.0258 mole) was heated to reflux (118° C.) for 35 minutes under argon. The mixture was cooled to 70° C., potassium permanganate (1.03 g, 6.48 mmol) was added portionwise and the mixture was heated to reflux for 60 minutes and then cooled to 30° C. To this solution was added (3S-trans)-3-[[[2-(formylamino)-4-thiazolyl]acetyl]amino]-4-methyl-2-oxo-1-azetidinesulfonic acid, potassium salt (5.8 g, 13 mmol) and this mixture was stirred at 30° C. while a slow stream (2–10 ml/min.) of air was passed through. The reaction was monitored by tlc for completion (silica gel plates, solvent system=ethylacetate:acetonitrile:water:acetic acid, 4:4:1:1; product $R_f$=0.6). After the thick reaction mixture was centrifuged and the solids were washed with cold glacial acetic acid (30 ml) and absolute ethanol (20 ml) and dried in vacuo to give a first crop of 3.55 g of the title compound.

EXAMPLE 2
(3S-trans)-3-[[[2-(t-Butoxycarbonylamino)-4-thiazolyl]oxoacetyl]amino]-4-methyl-2-oxo-1-azetidinesulfonic acid, potassium salt

(A)
(3S-trans)-3-[[[2-(t-Butoxycarbonylamino)-4-thiazolyl]acetyl]amino]-4-methyl-2-oxo-1-azetidinesulfonic acid, potassium salt To a solution of triethylamine (5.1 ml, 36 mmol) and 2-(t-butoxycarbonyl-amino)-4-thiazolylacetic acid (7.74 g, 30 mmol in methylene chloride (80 ml) at −10° C. was added a solution of pivaloyl chloride (4.5 ml, 36 mmol) in methylene chloride (20 ml) over 15 minutes. To the above mixture was then added, in a steady stream over 5 minutes, a solution of (3S-trans)-3-amino-4-methyl-2-oxo-1-azetidinesulfonic acid (5.4 g, 30 mmol), triethylamine (4.65 ml, 33 mmol) and pyridine (2.85 ml, 36 mmol) in acetonitrile (50 ml) at −10° C.; the mixture was allowed to warm to ambient temperature with stirring. After removal of the solvents in vacuo, the residue was dissolved in 10% aqueous tetrabutylammonium hydrogensulfate (100 ml, preadjusted to pH 3.5 with potassium bicarbonate) and extracted with methylene chloride (200 ml). The organic layer was dried over sodium sulfate, filtered and evaporated to dryness to yield 16.3 g of the title compound as the tetrabutylammonium salt.

The above salt was dissolved in acetone (75 ml), treated with a solution of potassium perfluorobutanesulfonate (8.45 g, 25 mmol) in acetone (75 ml), stirred at room temperature for 1 hour, and the solvents removed in vacuo. The residue was partitioned between water (75 ml) and methylene chloride-ethyl acetate (1:2, 225 ml), and the aqueous layer was lyophilized to afford 11.68 gm of the title compound.

(B)
(3S-trans)-3-[[[2-(t-Butoxycarbonylamino)-4-thiazolyl]oxoacetyl]amino]-4-methyl-2-oxo-1-azetidinesulfonic acid, potassium salt To a suspension of selenium dioxide (0.225 g) and powdered 4 Å molecular sieves (1.0 g) in dioxane (5.0 ml), a solution of (3S-trans)-3-[[[2-(t-butoxycarbonylamino)-4-thiazolyl]acetyl]amino]-4-methyl-2-oxo-1-azetidinesulfonic acid, tetrabutylammonium salt (1.322 g, 2 mmol) in dioxane (2.0 ml) was added. The mixture was heated to 100° C. for 0.5 hours and cooled to room temperature. The cooled mixture was filtered through Celite and the filtrate was concentrated to a dense oily residue (1.65 g) which was dissolved in acetone (5.0 ml) and treated with a solution of potassium perfluorobutanesulfonate (0.5 g) in acetone (5 ml). The resulting precipitate was collected, washed with acetone and then ether and dried under vacuum to give 0.5 g of the title compound.

(C)
(3S-trans)-3-[[[2-(t-Butoxycabonylamino)-4-thiazolyl]oxoacetyl]amino]-4-methyl-2-oxo-1-azetidinesulfonic acid, potassium salt (alternate oxidation)

To a filtered solution of manganic acetate dihydrate (3.48 g, 13 mmol) in glacial acetic acid (50 ml) was added (3S-trans)-3-[[[2-(t-butoxycarbonylamino)-4-thiazolyl]acetyl]amino]-4-methyl-2-oxo-1-azetidinesulfonic acid, tetrabutylammonium salt (17.15 g, 26.5 mmol) and the mixture was stirred at 35° C. under a slow air flow for 24 hours. The resulting mixture was diluted with 0.5M monobasic potassium phosphate (75 ml) and extracted with methylene chloride (200 ml). The organic layer was concentrated in vacuo and taken up in ethyl acetate (150 ml), washed with water (three 50 ml portions) dried over magnesium sulfate and the solvent was removed in vacuo. The residue was dissolved in acetone (50 ml) and treated with a solution of potassium perfluorobutanesulfonate (8.45 g, 25 mmol) in acetone (50 ml) and was stirred at ambient temperature for one hour. The solvents were removed in vacuo, replaced with methylene chloride-ethyl acetate (1:2, 300 ml) and the organic solution was extracted with water (75 ml). Removal of the water under reduced pressure and drying of the residue over phosphorous pentoxide under vacuum (0.5 mm Hg) for 15 hours afforded the title compound (8.13 g).

What is claimed is:

1. A process for preparing a compound having the formula

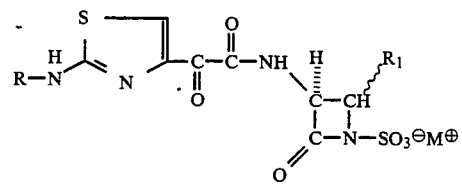

which comprises coupling a compound having the formula

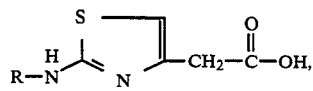

or a salt thereof, with a compound having the formula

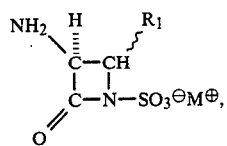

to yield a compound having the formula

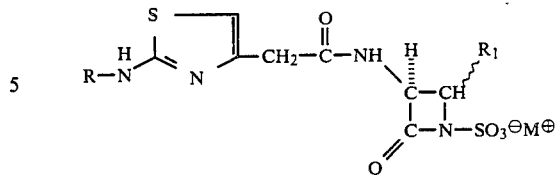

and oxidizing that compound to yield the desired compound; wherein
R is hydrogen or an amino protecting group;
$R_1$ is hydrogen, methyl or ethyl;
$M^\oplus$ is an inorganic cation or a substituted ammonium ion; and
$M_1^\oplus$ is hydrogen, an inorganic cation, or a substituted ammonium ion.

2. A process in accordance with claim 1 wherein R is an amino protecting group.

3. A process in accordance with claim 1 wherein $R_1$ is hydrogen.

4. A process in accordance with claim 1 wherein $R_1$ is α-methyl.

5. A process in accordance with claim 2 wherein R is formyl.

* * * * *